United States Patent [19]
Aebersold

[11] Patent Number: 5,240,859
[45] Date of Patent: Aug. 31, 1993

[54] METHODS FOR AMINO ACID SEQUENCING OF A POLYPEPTIDE

[75] Inventor: Rudolf H. Aebersold, Vancouver, Canada

[73] Assignee: B.R. Centre Limited, Vancouver, Canada

[21] Appl. No.: 658,403

[22] Filed: Feb. 22, 1991

[51] Int. Cl.$^5$ .................. G01N 1/28; G01N 24/00
[52] U.S. Cl. .................. 436/89; 436/161; 436/173; 530/402; 530/417; 530/337
[58] Field of Search .................. 436/89, 161, 173; 530/334–337, 412, 417, 402

[56] References Cited

U.S. PATENT DOCUMENTS 4,548,904  10/1985  Kent et al. .................. 436/89
4,820,648  4/1989  Caprioli et al. .................. 436/89

OTHER PUBLICATIONS

Machleidt et al., "New Supports in Solid-Phase Sequencing," *Methods in Enzymology*, pp. 263–277.
Aebersold et al., "Covalent Attachment of Peptides for High Sensitivity Solid-Phase Sequence Analysis," *Anal. Biochem.* 187:56–65, 1990.
Aebersold et al., "Electroblotting onto Activated Glass," *J. Biol. Chem.* 261(9):4229–4238, 1986.
Aebersold et al., "Covalent Immobilization of Proteins for High-Sensitivity Sequence Analysis: Electroblotting onto Chemically Activated Glass from Sodium Dodecyl Sulfate–Polyacrylamide Gels," *Biochem.* 27:6860–6867, 1988.
L'Italien et al., "Application of High-Performance Liquid Chromatographic Peptide Purification to Protein Microsequencing by Solid-Phase Edman Degradation," *Anal. Biochem.* 127:198–212, 1982.
Sanger and Tuppy, *Biochem. J.* 49:463–490, 1961.
Sanger and Thompson, *Biochem. J.* 53:353–374 1963).
Gray and Hartley, *Biochem. J.* 89:379–380, 1963).
Edman, *Acta Chem. Scand.* 4:283, 1950).
Edman and Begg, *Eur. J. Biochem.* 1:80–91, 1967.

*Primary Examiner*—James C. Housel
*Assistant Examiner*—David Redding
*Attorney, Agent, or Firm*—Seed and Berry

[57] ABSTRACT

The present invention provides methods and reagents for sequencing amino acids. One embodiment of the method for determining the terminal amino acid of a substantialy pure polypeptide comprises the steps of (a) attaching the polypeptide to a solid support, (b) reacting the polypeptide with a compound described below, under conditions and for a time sufficient for coupling to occur between the terminal amino acid of the polypeptide and the compound, thereby yielding a polypeptide with a derivatized terminal amino acid, (c) washing the solid support to remove unbound material, (d) cleaving the derivatized terminal amino acid from the polypeptide with a cleaving agent, (e) ionizing the cleaved derivatized terminal amino acid, and (f) determining the molecular weight of the derivatized terminal amino acid, such that the terminal amino acid is determined.

Within one embodiment, the compound is p-isothiocyanato phenethyl trimethylammonium and counterion salts thereof.

5 Claims, 9 Drawing Sheets

Predicted molecular weight for common amino acid PETMA-PITC phenylthiohydantoin derivitives

| Amino Acid | M.W. |
|---|---|
| Alanine | 292 |
| Valine | 320 |
| Leucine | 334 |
| Isoleucine | 334 |
| Proline | 318 |
| Phenylalanine | 368 |
| Tryptophan | 407 |
| Methionine | 352 |
| Glycine | 278 |
| Serine | 308 |
| Threonine | 322 |
| Cysteine | 324 |
| Tyrosine | 384 |
| Asparagine | 335 |
| Glutamine | 349 |
| Aspartic Acid | 336 |
| Glutamic Acid | 350 |
| Lysine | 349 |
| Arginine | 377 |
| Histidine | 358 |

Figure 9

METHODS FOR AMINO ACID SEQUENCING OF A POLYPEPTIDE

TECHNICAL FIELD

The present invention relates generally to proteins or polypeptides, and more specifically, to compounds and methods which may be utilized to determine the amino acid sequence of a protein or polypeptide.

BACKGROUND OF THE INVENTION

Proteins are among the most abundant of organic molecules, often encompassing as much as 50 percent or more of a living organisms dry weight. Proteins perform many different functions within a living organism. For example, structural proteins are often woven together in long polymers of peptide chains to form fibrils, which are a major constituent of skin, tendon, ligaments, and cartilage. Proteins also have biological functions, including, for example, regulatory proteins such as insulin or growth hormones, protective proteins such as antibodies or complement, and transport proteins such as hemoglobin and myoglobin. Many proteins are present only in very minute quantities within living organisms, yet are nevertheless critical to the life of the organism. For example, loss of Factor VIII in humans leads to hemophilia, or the inability to properly clot blood.

Scientists have learned how to synthesize or express specific proteins in order to therapeutically replace those proteins in individuals who are deficient or lacking in the production of a particular protein. In order, however, to express these proteins from cells, or to artificially synthesize these proteins, it is first often necessary to determine the amino acid sequence of the protein.

Due in part to the great diversity of amino acids (there are at least 20 different types found in naturally occurring proteins), it has been very difficult to develop techniques suitable for sequencing proteins. This is partially due to the fact that some proteins may only be obtained in very small amounts. Thus, there has been a continuing need for improved sensitivity in determining the sequence of amino acids in a protein.

Various methods have been suggested for the sequencing of proteins. The first useful method for determining the amino-terminal (N-terminal) of proteins was developed by Sanger, who found that the free, unprotonated alpha-amino group of peptides reacts with 2,4-dinitrofluorobenzene (DNFB) to form yellow 2,4-dinitrophenyl derivatives (see Sanger and Tuppy, *Biochem. J.* 49:463-490, 1961, see also Sanger and Thompson, *Biochem. J.* 53:353-374, 1963). Later methods were developed utilizing 1-dimethylaminonaphthalene-5-sulfonyl chloride (dansyl chloride), (see Gray and Hartley, *Biochem. J.* 89:379-380, 1963) resulting in a 100-fold increase in sensitivity over Sanger's method. One difficulty with this method, however, is that it could only be performed once with the same sample of protein because the acid hydrolysis step destroys the protein, preventing analysis beyond the amino terminal amino acid of the protein.

In order to determine the identity of amino acids beyond the N-terminal amino acid residue, a widely used method for labelling N-terminal amino acids (see Edman, *Acta Chem. Scand.* 4:283, 1950) was applied to sequencing proteins. This method utilized phenylisothiocyanate to react with the free amino group of a protein, to yield the corresponding phenylthiocarbamoyl protein. Upon treatment with an anhydrous acid, the N-terminal amino acid is split off as a anilinothiazolinone amino acid, which is then converted to the corresponding phenylthiohydantoin (PTH) derivative. This PTH derivative may then be separated, and analyzed by, for example, liquid chromatography. Utilizing this method (Edman degradation), repetitive cycles could be performed on a given peptide allowing the determination of as many as 70 residues in an automated instrument called a sequenator (see Edman and Begg, *Eur. J. Biochem.* 1:80-91, 1967).

Currently, protein sequences are almost universally determined by Edman degradation utilizing the reagent phenylisothiocyanate. The efficiency and sensitivity of this process is, however, currently limited by the ability of UV absorption to detect PTHs. Presently, the most sensitive way to perform the Edman degradation is gas-liquid phase sequence analysis, where the polypeptides are non-covalently absorbed to a support in a sequenator cartridge. This sequencing method allows the analysis of protein and peptide sequences at the 10-20 picomole level. To reach that sensitivity level, the degradation chemistry must be tuned to an extent which does not allow for the recovery of PTH derivatives of post-translationally modified amino acids such as phosphate esters of serine, threonine, or tyrosine residues. Even in cases where the site of post-translational modifications can be determined, with very few exceptions, the nature of such modifications is generally not determinable. Current methods for determining the sites and nature of post-translational modification lag in sensitivity by approximately a factor of a thousand as compared to the capability of determining partial sequences. In addition, due to the complicated procedures for efficiently extracting contaminants and reaction by-products, the gas-liquid phase sequencing mode is prohibitively slow, requiring a cycle time of 45 to 60 minutes.

There is, therefore, a need in the art for improved methods of sequencing proteins or peptides which are present only in small quantities. The present invention provides such a method, in part through the repetitive sequencing of extremely small quantities of proteins or peptides (i.e., in the femtomole ($10^{-15}$ moles) range), and further provides other related advantages.

SUMMARY OF THE INVENTION

The present invention provides compounds and methods suitable for microsequencing very small quantities of polypeptides. Within one aspect of the present invention, a compound is provided, comprising, (a) an isothiocyanate group, (b) an ionizable group capable of detection by mass-spectrometry, and (c) a linker connecting the isothiocyanate group with the ionizable group. In one embodiment, the ionizable group is a strongly basic group discussed in more detail below. In another embodiment, the ionizable group is a strongly acidic group. In a preferred embodiment of the present invention, the compound is p-isothiocyanato phenethyl trimethylammonium and counterion salts thereof. Representative counterion salts include halides such as iodide, bromide, chloride and fluoride, and cations of acetate or trifluoroacetate.

Within another aspect of the present invention, a method for determining the terminal amino acid of a substantially pure polypeptide is provided, comprising the steps of (a) attaching the polypeptide to a solid support, (b) reacting the polypeptide with a compound as discussed above, under conditions and for a time sufficient for coupling to occur between the terminal amino acid of the polypeptide and the compound, thereby yielding a polypeptide with a derivatized terminal amino acid, (c) washing the solid support to remove unbound material, (d) cleaving the derivatized terminal amino acid from the polypeptide with a cleaving agent, (e) ionizing the cleaved derivatized terminal amino acid, and (f) determining the molecular weight of the derivatized terminal amino acid, such that the identity of the terminal amino acid is determined. Within one embodiment, subsequent to the step of determining the molecular weight of the derivatized terminal amino acid, steps (b) through (f) are repeated such that the next amino acid is determined.

The present invention also provides a method for determining the amino acid sequence of a substantially pure polypeptide comprising the steps of (a) attaching the polypeptide to a solid support; (b) reacting the polypeptide with a compound as described above, under conditions and for a time sufficient for coupling to occur between the terminal amino acid of the polypeptide and the compound, thereby yielding a polypeptide with a derivatized terminal amino acid; (c) washing the solid support to remove unbound material; (d) cleaving the derivatized terminal amino acid from the polypeptide with a cleaving agent; (e) ionizing the cleaved derivatized terminal amino acid; (f) determining the molecular weight of the derivatized terminal amino acid; and (g) repeating steps (b) through (f) as recited above in order to determine the amino acid sequence of the polypeptide.

Within a preferred embodiment, subsequent to the step of cleaving, the derivatized terminal amino acid is resolved such that derivatized amino acids with identical molecular weights (such as leucine and isoleucine) are separated.

These and other aspects of the present invention will become evident upon reference to the following detailed description and attached drawings.

DETAILED DESCRIPTION OF THE INVENTION

As noted above, the present invention provides compounds and methods for sequencing very small quantities of protein or polypeptide. Within the context of the present invention, the term "polypeptide" is understood to include proteins as well as peptide chains of 2 or more amino acids. Generally, a compound of the present invention comprises (a) an isothiocyanate group, (b) an ionizable group capable of detection by mass spectrometry, and (c) a linker connecting the isothiocyanate group with the ionizable group.

Isothiocyanate groups ($N=C=S$) of the present invention are well known in the art (see Doolittle, "An Anecdotal Account of the History of Peptide Stepwise Degradation Procedures", *Methods in Protein Sequence Analysis*, Elzinga (ed.), Humana Press, Clifton, N.J.). The isothiocyanate group is the functional group of the compound, and is reacted with the N-terminal amino acid from a polypeptide under basic conditions, such that a thiocarbamoyl derivative is formed (see Edman, *Acta Chem. Scand.* 4:283, 1950). As discussed in more detail below, this derivative is then cleaved from the polypeptide, preferably with an acidic cleaving agent.

The isothiocyanate group is separated from the ionizable group by a linker. The linker is designed such that it is chemically stable and inert, and such that it allows for the efficient separation of the isothiocyanate group and the ionizable group (i.e. allows the isothiocyanate group and ionizable group to react independently). Preferably, the linker is composed of a phenyl ring, and a hydrocarbon chain. The phenyl ring, which is positioned next to the isothiocyanate group, has a desirable electronic structure which allows for optimal coupling and cyclization/cleavage rates. The hydrocarbon chain which is positioned next to the ionizable group provides additional separation between the ionizable group and the isothiocyanate group. As will be understood by one of ordinary skill in the art, a virtually limitless array of hydrocarbon chains and modified hydrocarbon chains may be utilized within the present invention. Preferred hydrocarbon chains which are attached to the phenyl ring may be found in the family of alkanes, with particularly preferred linkers ranging from 2 carbon atoms to about 20 carbon atoms in length. Within a preferred embodiment of the invention, the linker is a phenethyl group.

As noted above, the ionizable group is selected such that it is capable of detection by mass spectrometry. Within the context of the present invention, groups which are 0.1% to 1% ionizable are preferred; groups which are 1% to 10% ionizable are particularly preferred; and groups which are greater than 10% ionizable are most particularly preferred. A particularly preferred compound, p-isothiocyanato phenethyl trimethyl ammonium chloride (PETMA-PITC) is 10% to 50% ionizable. Such ionization efficiencies may be readily calculated by one of ordinary skill in the art utilizing standard techniques (see Smith et al., *Anal. Chem.* 60:1948, 1988).

Many different compounds are ionizable, and thus suitable for detection by mass spectrometry, including, for example, the salts of strong acids or strong bases. Within the context of the present invention, a "strong acid" includes those acids with a pKa of less than 4, preferably less than 2, and most preferably less than 1. A "strong base" includes those with a pKa of greater than 8, preferably greater than 10, and most preferably greater than 12. Representative examples of salts of strong acids include phosphate salts such as sodium phosphate and potassium phosphate, sulfate salts such as sodium sulfate, potassium sulfate, ammonium sulfate, or sulfonates such as potassium sulfonate. Representative examples of salts of strong bases include ammonium salts such as ammonium chloride, and quaternary amines such as trimethylammonium chloride. As will be understood by one of ordinary skill in the art, the strong acids or bases discussed above are accompanied by various counterion salts. For example, within various embodiments the counterion salt for an acid may be sodium or potassium. In like manner, many counterion salts for strong bases, such as trimethylammonium are known. representative examples include halides such as fluoride, chloride, bromide, or iodide, or cations of acetate or trifluoroacetate.

Once the isothiocyanate group, linker, and ionizable groups have been selected, the final compound may be synthesized by one of ordinary skill in the art utilizing standard organic chemistry reactions. As noted above, a preferred compound for use within the present invention is PETMA-PITC. This compound retains the excellent characteristics of phenylisothiocyanate in the coupling and cyclization/cleavage reactions of Edman degradation. Furthermore, the compound performs well in Edman-type chemistry because the electron structure of the phenyl ring is sufficiently separated from the quaternary ammonium group by the ethyl linker, thus allowing the isothiocyanate to react undisturbed by the quaternary ammonium group. Preparation of PETMA-PITC is described below in Example 1.

The coupling and cyclization/cleavage rates of the compound may be tested to ensure that the compound is suitable for sequencing polypeptides. As an example, measurement of coupling and cyclization/cleavage rates for the compound PETMA-PITC is set forth below in Example 2. In general, the faster the coupling rate the more preferred the compound. Coupling rates of between 2 and 10 minutes at 50° C. to 70° C. are particularly preferred. Compounds which take longer than 15 minutes for complete coupling are less desirable due to the length of time it would take to run several sequential amino acid degradation reactions. Similarly, fast cyclization/cleavage rates are also preferred, because exposure to an acid over an extended period of time will hydrolyze the peptide bonds in the polypeptide. Preferably, the cyclization/cleavage reaction should be essentially complete in 5 minutes or less after incubation at 50° C.

Once a suitable compound has been selected, the compound may be utilized to determine the terminal amino acid of a substantially pure polypeptide. Briefly, this method comprises the steps of: (a) attaching the polypeptide to a solid support; (b) reacting the polypeptide with a compound as discussed above, under conditions and for a time sufficient for coupling to occur between the terminal amino acid of the polypeptide and the compound, thereby yielding a polypeptide with a derivatized terminal amino acid, (c) washing the solid support to remove unbound material, (d) cleaving the derivatized terminal amino acid from the polypeptide with a cleaving agent, (e) ionizing the cleaved derivatized terminal amino acid, and (f) determining the molecular weight of the derivatized terminal amino acid, such that the terminal amino acid is determined. Additionally, steps (b) through (f) may be repeated such that the entire amino acid sequence of the polypeptide is determined.

As noted above, this method may be utilized to determine the sequence of a substantially pure polypeptide. Within the context of the present invention, "substantially pure" means that the polypeptide is about 80% homogeneous, and preferably about 99% or greater homogenous. Many methods well known to those of ordinary skill in the art may be utilized to purify the polypeptide prior to determining its amino acid sequence. Representative examples include HPLC, Reverse Phase-High Pressure Liquid Chromatography (RP-HPLC), gel electrophoresis, chromatography, or any of a number of peptide purification methods (see generally the series of volumes entitled "Methods in Protein Sequence Analysis"). Gel electrophoresis (see Aebersold, *J. Biol. Chem.* 261(9):4229–4238, and RP-HPLC (see Aebersold, *Anal. Biochem.* 187:56–65, 1990) are particularly preferred purification methods. Additionally, for sequencing purposes, polypeptides of from 3 to 50 amino acids in length are preferred, with polypeptides from 10 to 30 amino acids being particularly preferred. Proteins or polypeptides may readily be cleaved into preferred lengths by many methods, including, for example, by chemical methods, by enzymatic methods, or by a combination of the two. Representative chemical compounds which may be utilized to cleave proteins or polypeptides include cyanogen bromide, BNPS-skatole and hydroxylamine (all available from Aldrich Chemical Company, Milwaukee, Wis.). Representative enzymes include trypsin, chymotrypsin, V8 protease, or Asp N (all available from Boehringer Mannheim Biochemicals, Indianapolis, Ind.). The mixture of cleaved fragments may then be separated into like sized fragments by various methods, including, for example: gel electrophoresis, HPLC, and RP-HPLC. Reversed-phase HPLC is particularly preferred for the separation of these fragments due to its capability of high resolution.

The substantially pure polypeptide is then attached to a solid support for protein sequencing. Various materials may be used as solid supports, including, for example, numerous resins, membranes or papers. These supports may additionally be derivatized to facilitate coupling. Supports which are particularly preferred include membranes such as Sequelon ™ Milligen/Biosearch, Burlington, Mass.). Representative materials for the construction of these supports include, among others, polystyrene, porous glass, and polyacrylamide. In particular, polystyrene supports include, among others: (1) a (2-aminoethyl) aminomethyl polystyrene (see Laursen, *J. Am. Chem. Soc.* 88:5344, 1966); (2) a polystyrene similar to number (1) with an aryl amino group (see Laursen, *Eur. J. Biochem.* 20:89, 1971); (3) amino polystyrene (see Laursen et al., *FEBS Lett.* 21:67, 1972); and (4) triethylenetetramine polystyrene (see Horn and Laursen, *FEBS Lett.* 36:285, 1973). Porous glass supports include: (1) 3-aminopropyl glass (see Wachter et al., *FEBS Lett.* 35:97, 1973); and (2) N-(2-aminoethyl)-3-aminopropyl glass (see Bridgen, *FEBS Lett.* 50:159, 1975). Reaction of these derivatized porous glass supports with p-phenylene diisothiocyanate leads to activated isothiocyanato glasses (see Wachter et al., supra). Polyacrylamide-based supports have also been utilized, including a cross-linked β-alanylhexamethylenediamine polydimethylacrylamide (see Atherton et al, *FEBS Lett.* 64:173, 1976), and an N-aminoethyl polyacrylamide (see Cavadore et al., *FEBS Lett.* 66:155, 1976).

One of ordinary skill in the art may then readily utilize appropriate chemistry to couple the polypeptide to the solid supports described above (see generally Machleidt and Wachter, *Methods in Enzymology:* [29] *New Supports in Solid-Phase Sequencing* 263-277, 1974). Preferred supports and coupling methods include the use of aminophenyl glass fiber paper with EDC coupling (see Aebersold et al. *Anal. Biochem.* 187:56-65, 1990); DITC glass filters (see Aebersold et al., *Biochem.* 27:6860-6867, 1988) and the membrane polyvinylidifluoride (PVDF) (Immobilon P TM, Milligen/Biosearch, Burlington, Mass.), along with SequeNet TM chemistry (see, Pappin et al., *Current Research in Protein Chemistry*, Villafranca J. ed., pp. 191-202, Academic Press, San Diego, 1990).

The polypeptide which is attached to the solid support may now be reacted with a compound as described above, under conditions and for a time sufficient for coupling to occur between the terminal amino acid of the polypeptide and the compound, thereby yielding a polypeptide with a derivatized terminal amino acid. As discussed above, it is preferred to conduct preliminary experiments with the compound to determine the preferred time and conditions in order to best effect coupling. In the case of PETMA-PITC, as demonstrated in Example 2A, 66% coupling was achieved with this compound at a concentration of 0.8%, after 20 minutes at 50° C. In a preferred embodiment of the present invention, the concentration of PETMA-PITC is increased to greater than 1%.

Preferably, coupling occurs under basic conditions, for example, in the presence of an organic base such as trimethyl amine, triethyl amine, or N-ethylmorpholine. In a preferred embodiment, the compound PETMA-PITC is allowed to couple with the bound polypeptide in the presence of 5% N-ethylmorpholine in methanol: $H_2O$ (75:25 v/v).

Subsequently, the solid support is washed to remove all unbound material, including uncoupled compound, excess coupling base, and reaction by-products. Various reagents are suitable as washing solvents, including, for example, methanol, water, a mixture of methanol and water, or acetone.

The derivatized terminal amino acid which is now bound to the compound may then be cleaved from the rest of the bound polypeptide, preferably with a strong acid which is utilized as the cleaving agent. Various strong acids are suitable for use within the present invention, including, for example, trifluoroacetic acid, heptafluorobutyric acid and hydrochloric acid. Within a preferred embodiment, 100% trifluoroacetic acid is utilized to cleave the derivatized terminal amino acid from the polypeptide.

Within the present invention, the cleaved derivatized terminal amino acid is then ionized, and the molecular weight determined by a mass spectrometer. Various mass spectrometers may be used within the present invention. Representative examples include: triple quadrupole mass spectrometers, magnetic sector instruments (magnetic tandem mass spectrometer, JEOL, Peabody, Mass.), and a Fourier Transform Ion Cyclotron Resonance Mass Spectrometer (Extrel Corp., Pittsburgh, Mass.). Within a preferred embodiment, a triple quadrupole mass-spectrometer with an electron-spray or ion-spray ionization source (model API III, SCIEX, Thornhil, Ontario, Canada) is utilized to ionize the derivatized terminal amino acid, and to determine its molecular weight. If the terminal amino acid is derivatized with the preferred compound PETMA-PITC, the ionizable group trimethylammonium chloride mediates excellent ionization in electron spray ionization sources. This compound allows detection of femtomole quantities of PETMA-PTH derivatives.

Within all embodiments described herein, the steps of reacting the polypeptide through determining the molecular weight of the derivatized terminal amino acid may be repeated such that the next amino acid in the polypeptide is determined.

Within one aspect of the present invention, the above methods are automated. Instruments such as the Milligen/Biosearch 6600 protein sequenator may be utilized along with the reagents discussed above to automatically sequence the polypeptide. This instrument has the necessary programming flexibility to develop new degradation cycles optimized for the novel compound. Cleaved PETMA-PTH derivatives may be collected in a fraction collector and submitted to off-line mass-spectrometric analysis, using a triple quadrupole mass-spectrometer, as discussed above.

In certain instances, it is preferable to include a step to further resolve amino acids of an identical molecular weight such as leucine or isoleucine, subsequent to cleaving the derivatized amino acid from the polypeptide. For high-sensitivity mass-spectrometric analysis of samples injected on-line from a separation system, the flow rate of the separating solvent is of crucial importance. Suitable methods in this regard include capillary electrophoresis, ion-exchange HPLC and RP-HPLC.

Capillary electrophoresis (CE) connected on-line to a mass spectrometer is a preferred method for resolving amino acid derivatives because: (1) CE has an extremely high resolving power, separations with several million theoretical plates have been documented; and (2) the solvent flow in CE separations is very low. The solvent flow in CE is induced by the electroosmotic effect. As a consequence, the flow is dependent on the pH of the solvent and additionally does not suffer from any "wall" or diffusion effects which disturb the separating power.

High-Pressure Liquid Chromatography (HPLC) or Reversed-Phase High-Pressure Liquid Chromatography (RP-HPLC) may also be utilized to resolve identical molecular weight amino acids. Briefly, within one embodiment the cleaved derivatized terminal amino acid is eluted from the automated sequentor as discussed above, and redissolved in 200 μl of transfer solution (see below). Between 10 and 100 μl per minute may be injected into an RP-HPLC, thus resolving amino acids of an identical molecular weight.

The following examples are offered by way of illustration, and not by way of limitation.

EXAMPLES

Unless otherwise stated, analysis of nmr spectra was performed with a Bruker HC-200 Spectrometer. Analysis of mass spectra was accomplished with a modified AEI-MS9 mass spectrometer (Kratos, Manchester, England). Analysis of infrared spectra was accomplished with a Perkin-Elmer 1710 Infrared Fourier Transform

Example 1

Preparation of PETMA-PITC (p-isothiocyanato phenethyl trimethylammonium chloride)

A. Preparation and Characterization of p-nitro phenethyl trimethyl ammonium Iodide Five grams (0.025 moles) of 4-nitrophenethylamine hydrochloride (Aldrich, Milwaukee, Wis.) was dissolved in 2 ml of deionized water. The solution was then diluted with 15 ml of acetone, and then treated with 4.6 g (0.33 mol) of $K_2CO_3$ and 10 ml (0.161 mols) of iodomethane (Aldrich, Milwaukee, Wis.). The solution was refluxed for 3 days. Solvent was then removed in vacuo, and the solid that remained was dissolved in excess hot ethanol and filtered.

The final product was recrystallized twice from ethanol to produce 7.5 g (a 91% yield). This product had a melting point of 189° C.-191° C. (compared to a literature value of 195° C.-196° C.), and produced the following nmr spectra:

$^1$H NMR: d($D_2O$) 8.21 (d, 2H, J=8 Hz) 7.52 (d, 2H, J=8 Hz) ($AA^1$ $BB^1$ pattern, Ar-H) 3.60 (m, 2H, $ArCH_2$), 3.30 (m, 2H, $CH_2N$), 3.18 (S, 9H, N—$CH_3$).

B. Preparation of P-amino phenethyl trimethylammonium Acetate

Four grams (0.12 mols) of the product from step A, above, was dissolved in 80 ml of 90% acetic acid. Six point four grams (0.098 mols) of zinc dust was added slowly over 10 minutes, then the reaction was stirred for 5 hours at room temperature. The solution was filtered and washed with 70% ethanol, followed by the addition of solid $Na_2CO_3$ until neutrality was achieved. The solvents were removed in vacuo and the solid was suspended in excess boiling methanol. The solution was hot filtered, and the filtrate was then evaporated to dryness. Following the same procedure, the remaining solid was then treated with acetone instead of methanol.

The solid was dissolved in water, filtered, then lyophilized overnight to produce 2.3 g (81% yield) of a tan solid. This product has a melting point of 200#C(d), infrared spectra of IR (KBr) 3393 (s,b), 3317(s), 1633(s), 1516(s), $cm^{-1}$, mass spectra of $M^+$179 (by Fast Atom Bombardment-"FAB", AEI-MS9), and produced the following nmr spectra:

$^1$H NMR: d($D_2O$) 7,15 (d, 2H, J=8 Hz) 6.82 (d, 2H, J=8 Hz) ($AA^1$ $BB^1$ pattern, Ar—H), 3.50 (m,2H, $ArCH_2$), 3.18 (S, 9H, N—$CH_3$) 3.02 (m, 2H, $CH_2N$), 1.85 (S, 3H, $CH_3COO^-$).

$^1$H NMR: d(DMSO-$D_6$) 4.96 (S, 2H, $NH_2$).

C. Preparation of p-isothiocyanato phenethyl trimethylammonium Chloride (PETMA-PITC)

PETMA-PITC was synthesized utilizing acetone as a solvent for thiophosgene in a procedure similar to that of Tsou (see U.S. Pat. No. 3,028,397). Briefly, 100 mg (0.42 mmols) of the final product from step B, above, was suspended in 5 ml of acetone, and treated with 0.1 ml (1.31 mmols) of thiophosgene and stirred for 2 days at room temperature. The reaction was stirred over AgX 1-8 ($OH^-$) resin (Dowex, Aldrich, Milwaukee, Wis.) for 5 minutes, then quenched with methanol. The solution was filtered and evaporated to a brown oil. The oil was purified by preparative thin layer chromatography utilizing a mixture of ethyl acetate, ethanol, and water (7:2:1).

The final product was a soapy white solid. The yield (30 mg, or 27.8%) was not particularly high due to the sample's retention of water (as detected by nmr), which was not removed by vacuum. The final product had a molecular mass of $M^+$222 (as determined by a SCIEX model API III triple quadrupole mass spectrometer equipped with an ion spray ion source), and the following infrared spectra: IB(KBr) 3369(s) 2128(s) 1516(m) $cm^{-1}$. The final product produced the following nmr spectra:

$^1$H NMR: d(Acetone $D_6$) 7.60 (d, 2H, J=8), 7.35 (d, 2H, J=8) ($AA^1$ $BB^1$ pattern, Ar—H), 4.00 (m, 2H, Ar—$CH_2$), 3.56 (S, 9H, N—$CH_3$), 3.35 (m, $CH_2$—N).

Larger preparative quantities of the final product were purified on a preparative reverse-phase HPLC column (Vydac C-18, Vydac, Hesperia, Calif.) 20×300 mm. Column buffers included 0.1% trifluoroacetic acid (TFA) in water and 0.1% TFA in a 70:30 mixture of acetonitrile and water. The product was detected by UV absorbance of 270 nm. The peak corresponding to the product was immediately frozen and lyophilized. The lyophilized product, presumably the trifluoroacetate salt of the compound, appeared as a fluffy, off-white powder and had the same physical constants as the product purified by TLC.

Example 2

Measurement of coupling and cleavage rates for PETMA-PITC

A 10-amino-acid decapeptide (hereinafter referred to as "ACP") containing the sequence Val Gln Ala Ala Ile Asp Tyr Ile Asp Gly (SEQ ID NO: 1) was synthesized by solid phase synthesis using an Applied Biosystem Synthesizer (Applied Biosystems, Foster City, Calif.), and purified by HPLC. This peptide was utilized in the following reactions in order to determine the coupling/cleavage rate of PETMA-PITC.

A. Measurement of the Coupling Rate of PETMA-PITC and a Decapeptide

Ten microliters of 1 mg/ml ACP, 30 μl of coupling buffer (containing 5% N-ethylmorpholine (Sigma) and 70% methanol), and 10 μl of PETMA-PITC in water (final conc. 0.8%) were placed into a small microfuge tube, and incubated at 50° C. in a heat block.

Samples were collected after 1, 2, 15, and 30 minutes, and immediately injected directly into an RP-HPLC system (Waters, Division of Millipore, Milford, Mass.) which utilized a Vydac C4 column (Vydac, Hesperia, Calif.). Column buffers included 0.1% trifluoroacetic acid (TFA) in water, and 0.1% TFA in a 70:30 mixture of acetonitrile and water.

Elution of peptide from the column was monitored at 214 nm. The degree of coupling was calculated based on the relative peak sizes of underivatized and derivatized peptides. The percentage coupling after 1, 2, 15 and 30 minutes is shown below in Table 1.

TABLE 1

| Time course of coupling reaction | |
|---|---|
| Time (min) | Coupling (%) |
| 1 | 6 |
| 2 | 10 |
| 15 | 50 |
| 20 | 66 |

The compound concentration (0.8%) used in this experiment was too low to achieve optimal coupling. Typically, compound concentrations in the range of 2-5% are generally preferred. Using comparable compound concentrations, the coupling kinetics observed with PETMA-PITC is comparable with the kinetics for phenylisothioscyanate (PITC), the standard protein sequencing compound.

B. Measurement of the Cyclization/Cleavage Rate of PETMA-PITC

A peak containing the ACP decapeptide derivatized with PETMA-PITC was isolated and divided into four aliquots which were dried by vacuum. Individual aliquots were then exposed to 20 μl of 100% TFA, and held at a temperature of 50° C. At times of 1, 2, and 5 minutes samples were diluted with 20 μl of water, and injected into a RP-HPLC. Progress of the cyclization/cleavage reaction was monitored by a shift in the retention time of the peak of the starting material to a product peak which eluted earlier in the chromatogram. As indicated below in Table 2, cleavage was essentially complete after 2 minutes.

TABLE 2

| Time (min) | Cleavage (%) |
|---|---|
| 1 | 85 |
| 2 | 94 |
| 5 | 92 |

Example 3

Detection of a PETMA-PTH amino acid derivatives in an Ion Spray Mass-Spectrometer Forty milligrams of PETMA-PITC (molecular weight=221.34 g/mole) was taken up in 1.8 ml of water to provide a stock solution of 100 nmoles/μl. One milligram of each amino acid (valine, alanine, isoleucine, and glycine) was placed into an eppendorf tube and dissolved in 100 μl of a mixture of water, methanol, ethyl acetate (49:50:1). The pH was then adjusted to 9.2 with triethylamine, resulting in a final amino acid concentration of 100 lmoles in 100 μl.

To each amino acid sample 10 μl of stock PETMA-PITC was added. The mixture was incubated at 50° C. for 15 minutes, and then dried by vacuum. Fifty microliters of 50% trifluoroacetic acid in water was added to the reaction mixture, which was then incubated at 50° C. for 30 minutes, and brought to dryness under vacuum. The products were then redissolved in 200 μl of water and HPLC purified on a gradient of 0–60% B (70% acetonitrile, 30% water, 0.1% TFA) over 20 minutes on an analytical HPLC system equipped with a Vydac C-18 column (4.6×300 mm) (Vydac, Hesperia, Calif.). The isolated purified PETMA-PTH derivatives were checked for concentration by UV spectrometry at 270 nm. Results are set forth below in Table 3.

TABLE 3

| | Valine | Alanine | Isoleucine | Glycine |
|---|---|---|---|---|
| Abs. | 0.40 | 0.41 | 0.27 | 0.55 |
| Ext. Coeff. | 14,000 | 14,000 | 14,000 | 14,000 |
| c(M) | $2.8 \times 10^{-5}$ | $2.9 \times 10^{-5}$ | $1.9 \times 10^{-5}$ | $3.9 \times 10^{-5}$ |
| nmoles | 43 | 44 | 29 | 59 |

The purified derivatized amino acids were infused at a rate of 2 μl per minute into a Triple Quadrupole Mass-Spectrometer (API III, Sciex, Thornbill, Ontario, Canada). The mass spectrometer was equipped with an ion spray ion source. The solvent for the infusion was 0.1% TFA in water.

Figure 1:
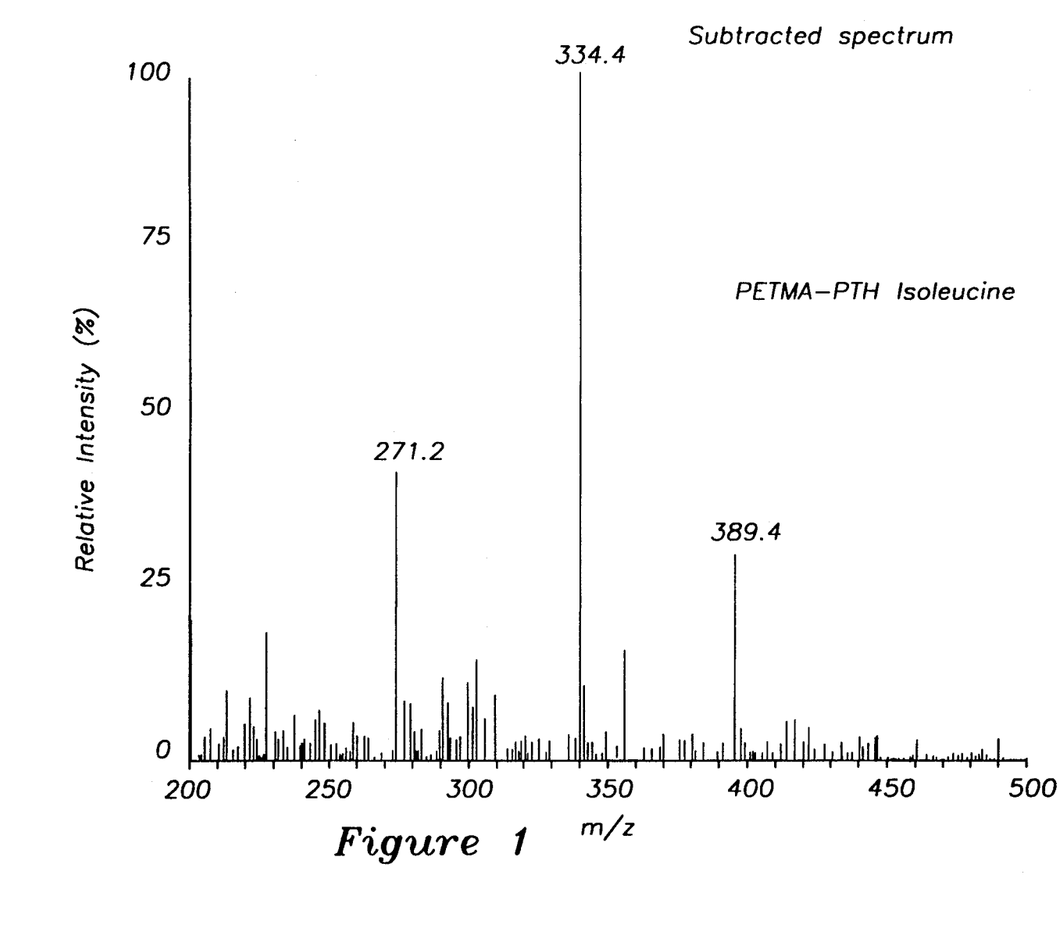
FIG. 1 illustrates the mass spectrum for the phenethyl thiohydantoyl trimethyl ammonium trifluoroacetate derivative of isoleucine.
Figure 2:
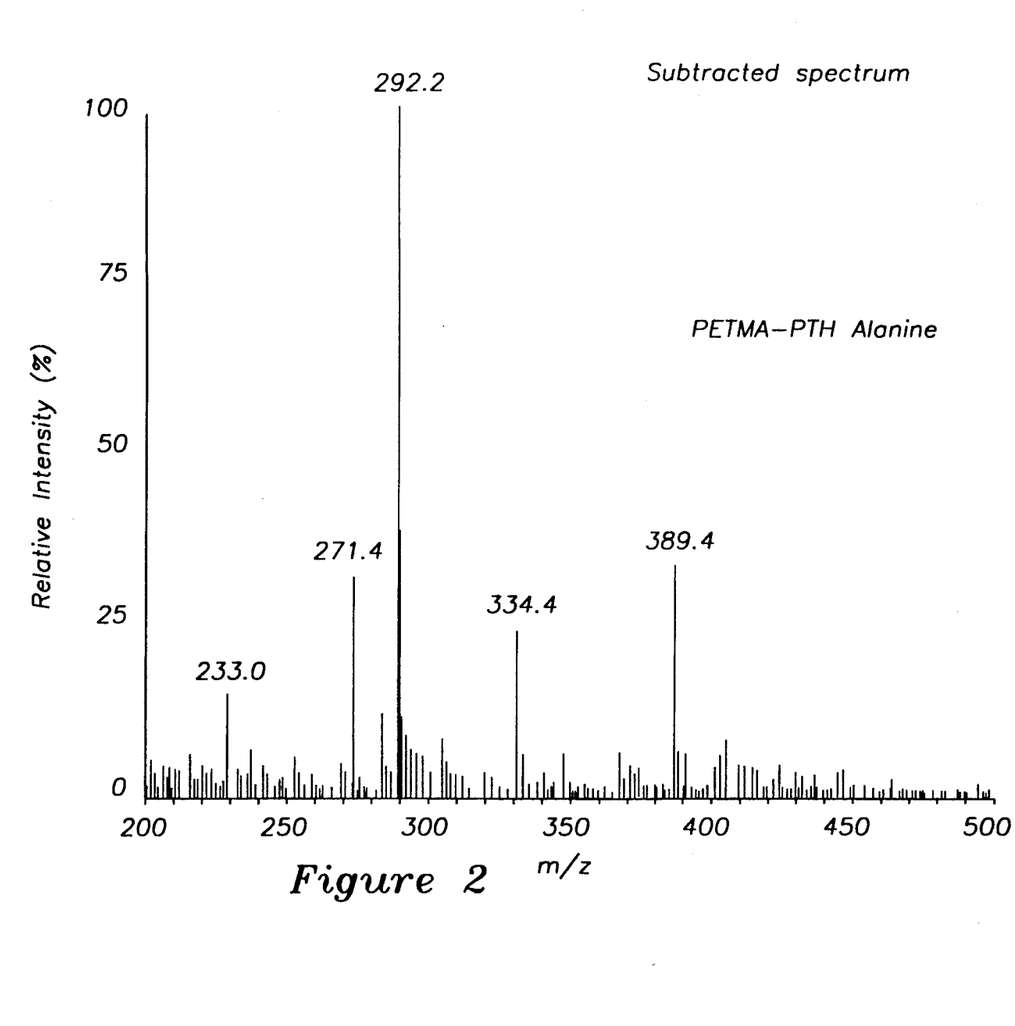
FIG. 2 illustrates the mass spectrum for the phenethyl thiohydantoyl trimethyl ammonium trifluoroacetate derivative of alanine.
Figure 3:
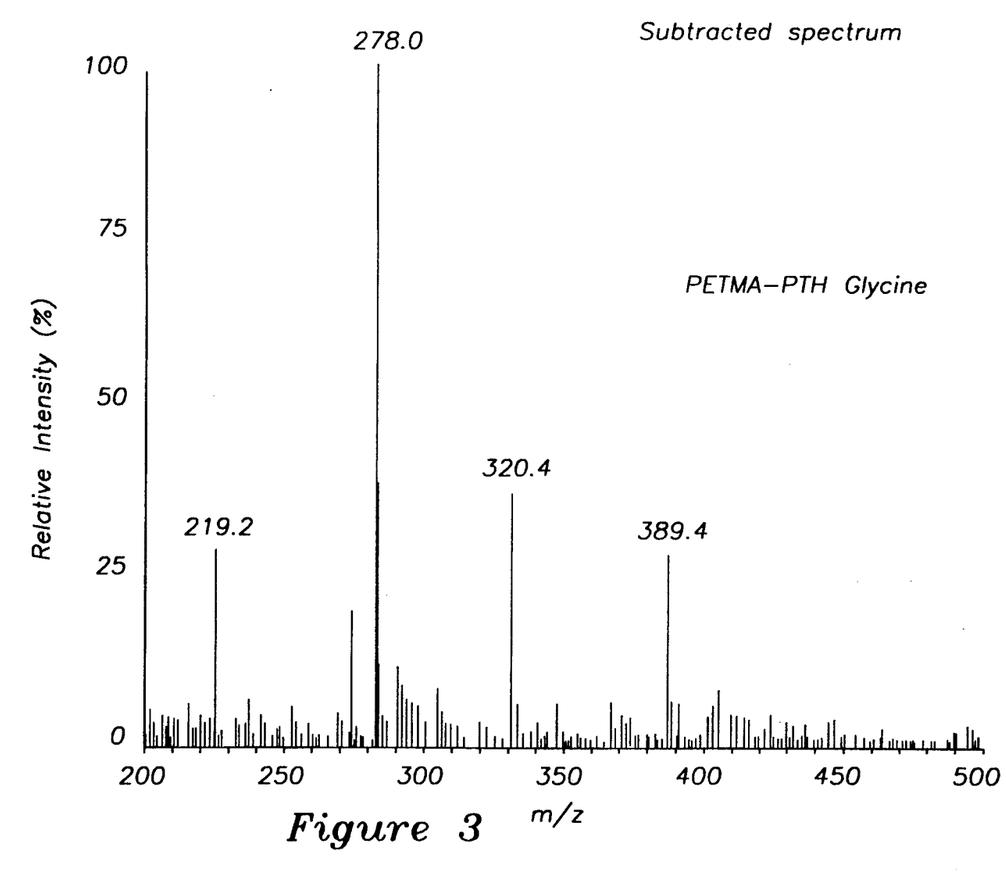
FIG. 3 illustrates the mass spectrum for the phenethyl thiohydantoyl trimethyl ammonium trifluoroacetate derivative of glycine.
Figure 4:
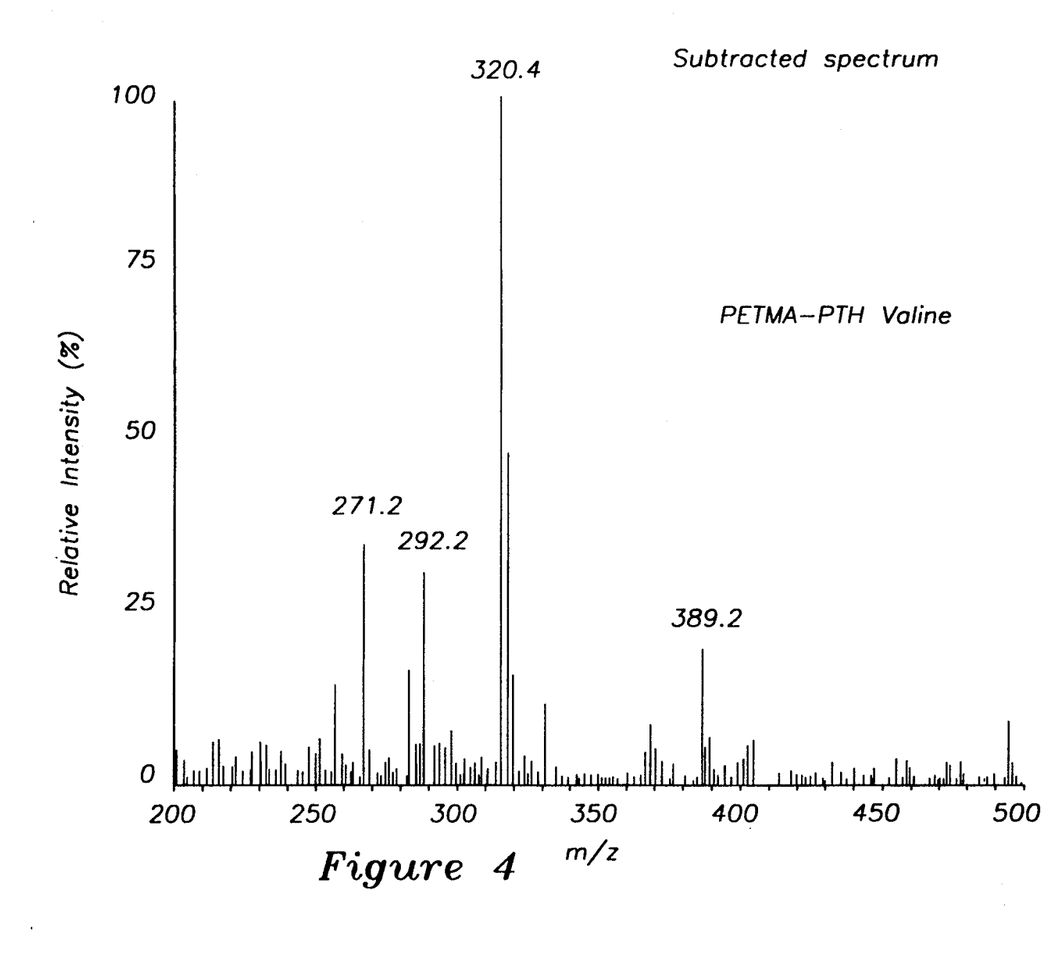
FIG. 4 illustrates the mass spectrum for the phenethyl thiohydantoyl trimethyl ammonium trifluoroacetate derivative of valine.
Figure 5:
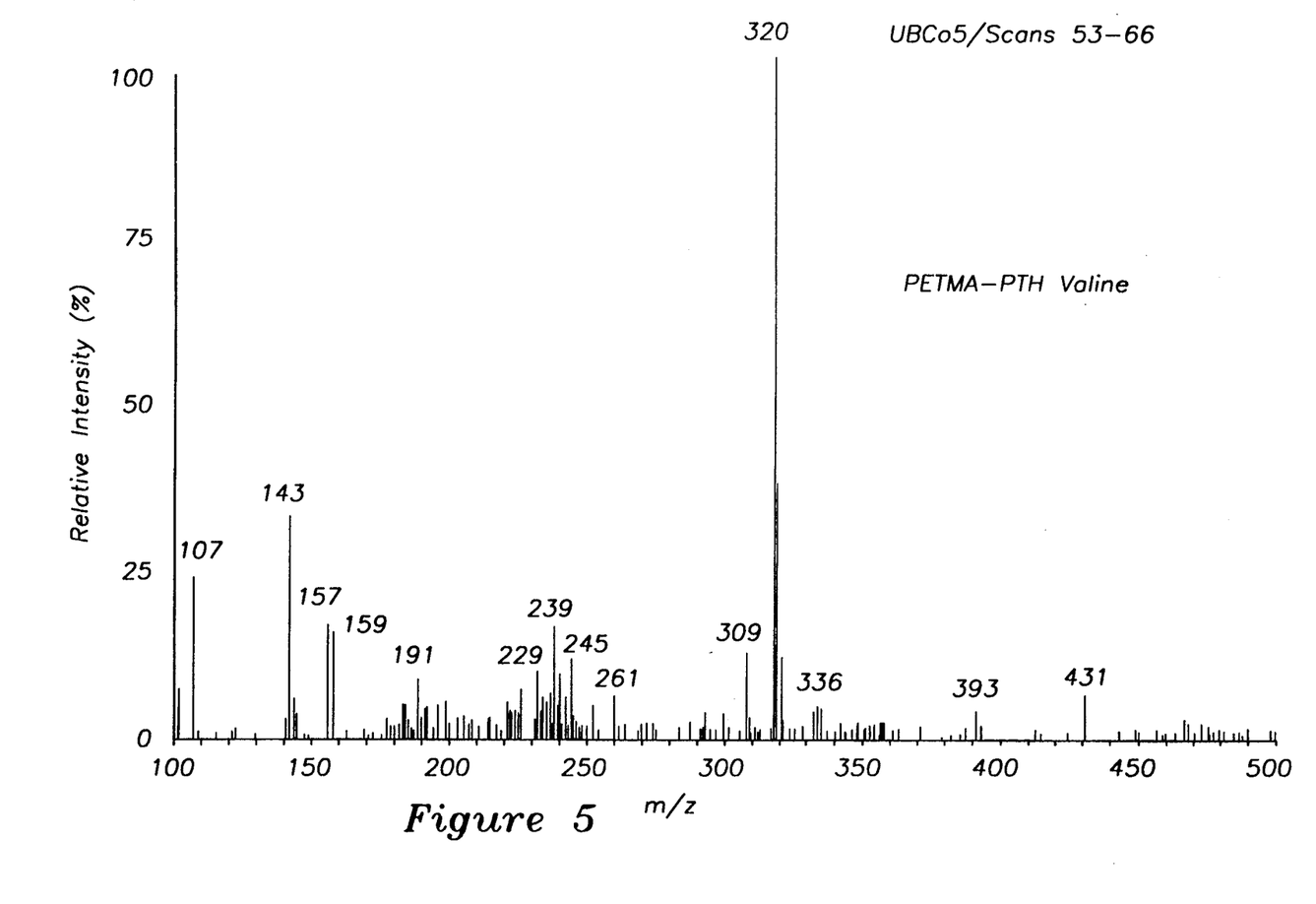
FIG. 5 illustrates the mass spectrum for 2.8 picomoles of the phenethyl thiohydantoyl trimethyl ammonium trifluoroacetate derivative of valine.
Figure 6:
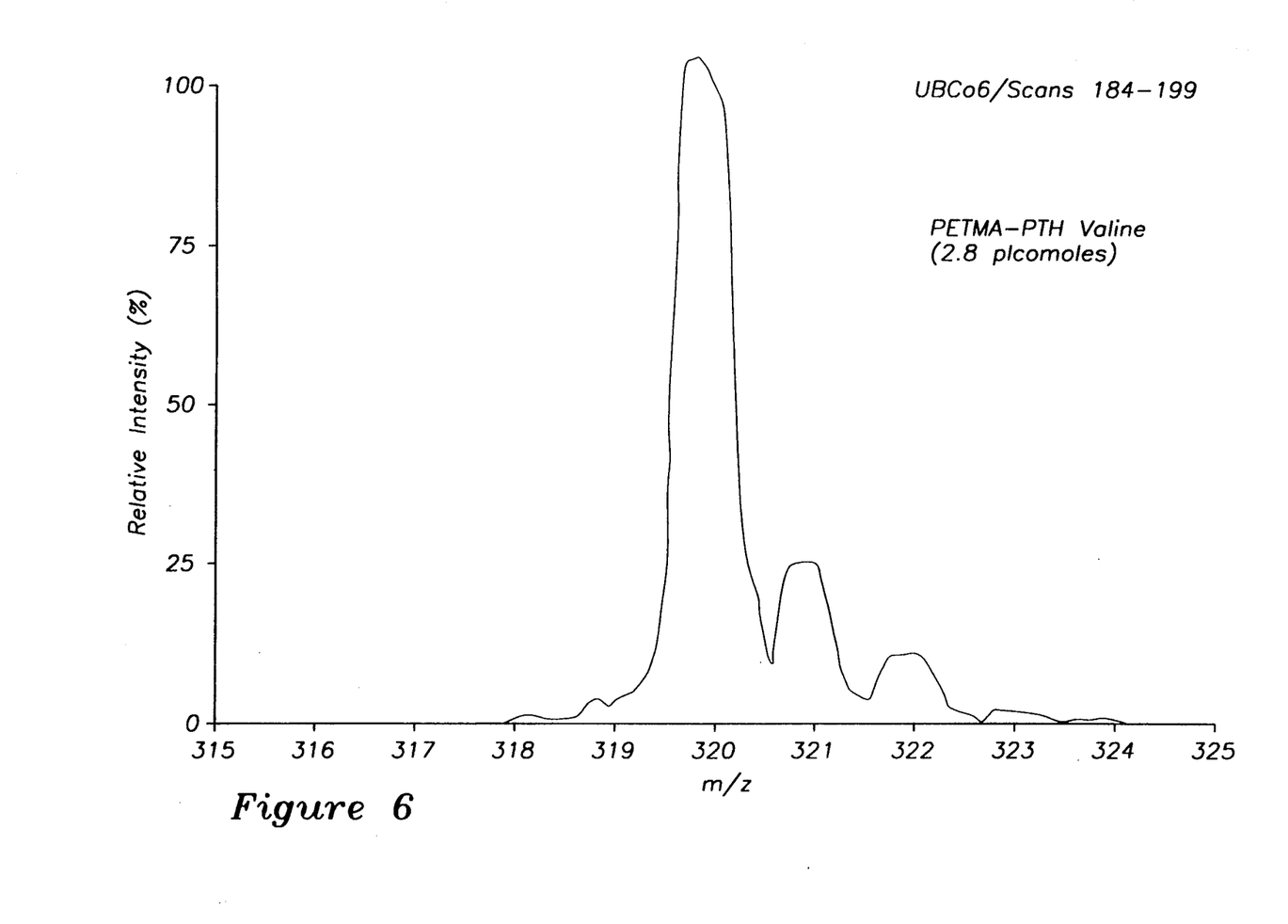
FIG. 6 illustrates the mass spectrum for 2.8 picomoles of the phenethyl thiohydantoyl trimethyl ammonium trifluoroacetate derivative of valine, for the mass range of 315 to 325 Da.
Figure 7:
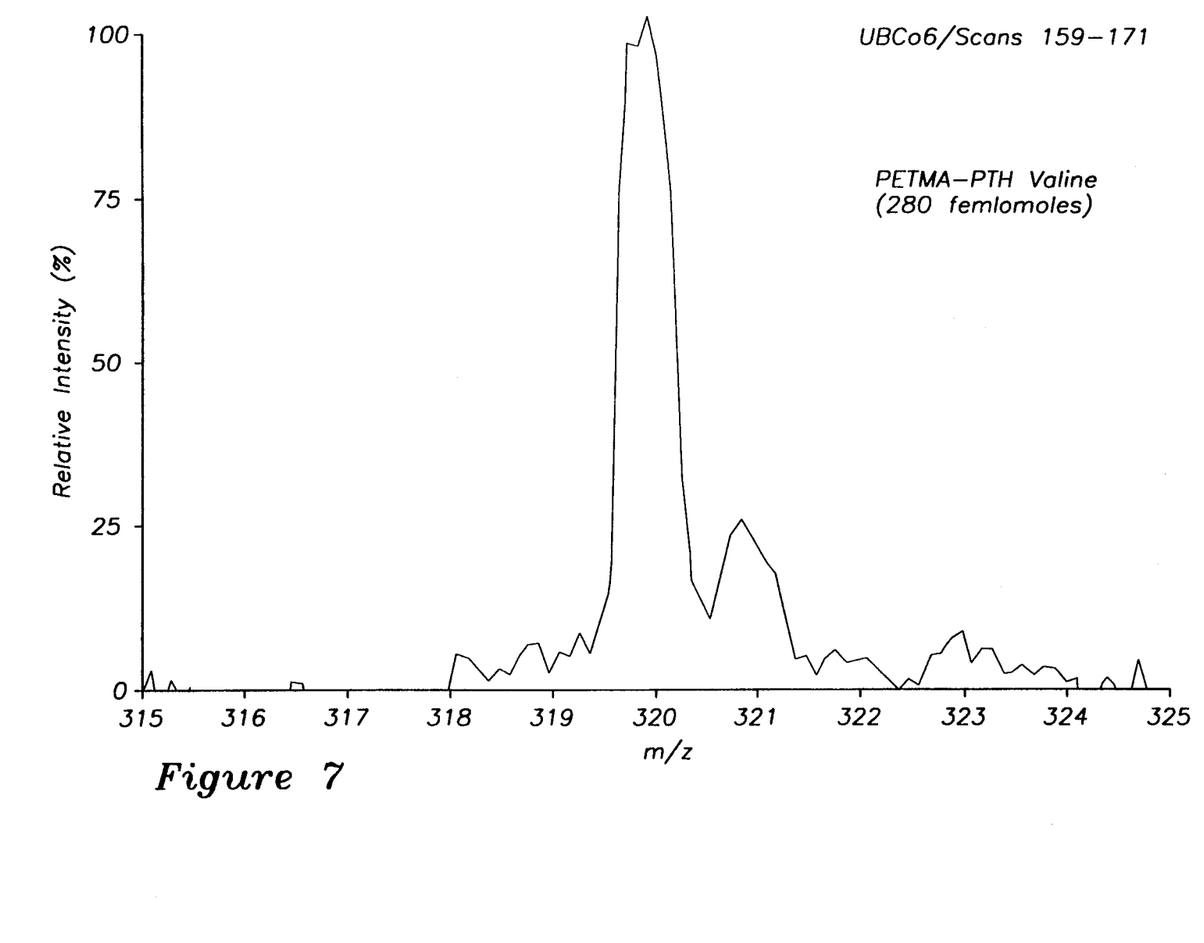
FIG. 7 illustrates the mass spectrum for 280 femtomoles of the phenethyl thiohydantoyl trimethyl ammonium trifluoroacetate derivative of valine, for the mass range of 315 to 325 Da.
Figure 8:
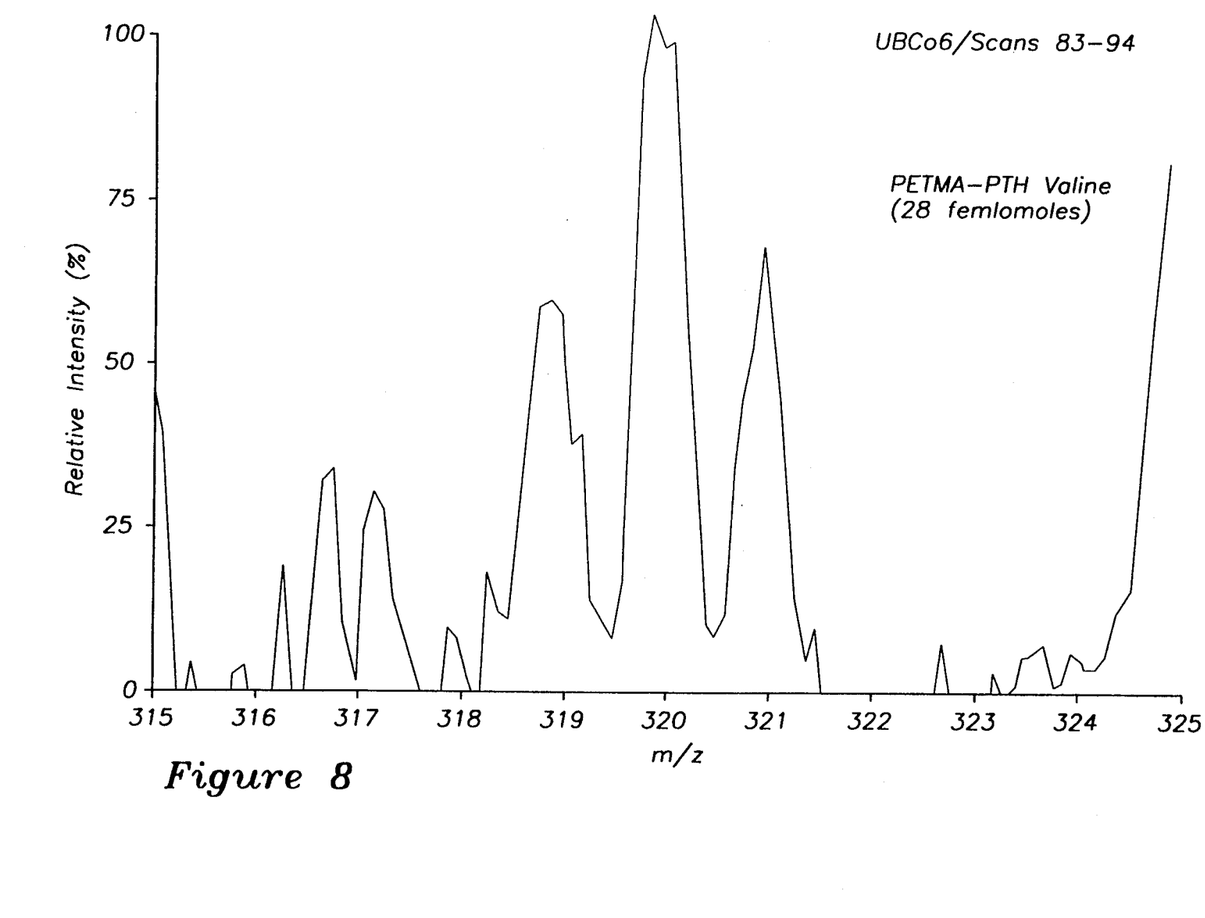
FIG. 8 illustrates the mass spectrum for 28 femtomoles of the phenethyl thiohydantoyl trimethyl ammonium trifluoroacetate derivative of valine, for the mass range of 315 to 325 Da.
Figure 9:
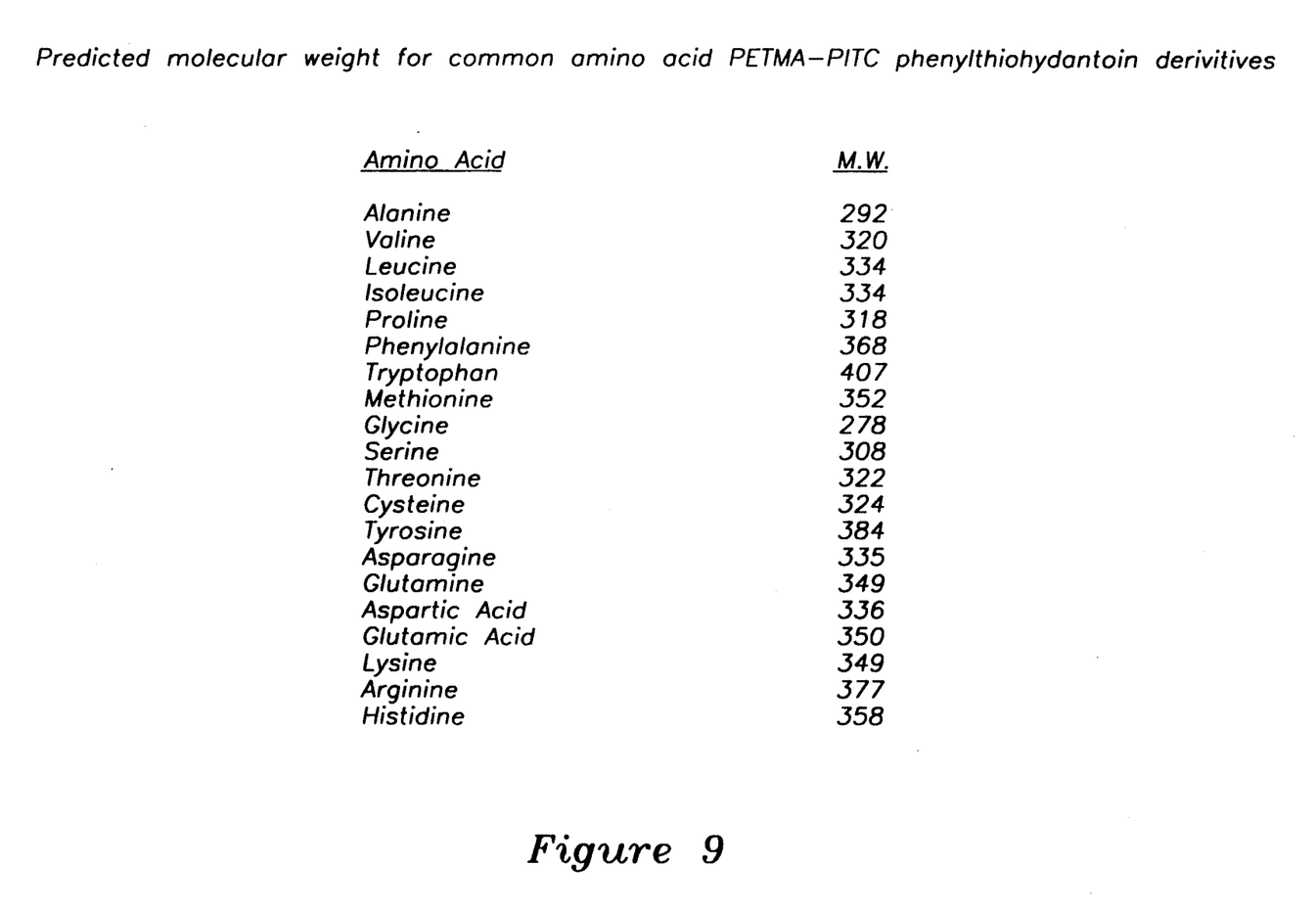
FIG. 9 is a table listing the predicted molecular weight for common amino acid PETMA phenylthiohydantoin (PETMA-PTH) derivatives.

Results of the experiments are provided in FIGS. 1 through 8. FIGS. 1 through 4 illustrate the mass spectra for isoleucine, alanine, glycine, and valine respectively. FIG. 5 illustrates the mass spectrum of valine at a 1:10 dilution (2.8 picomoles injected). FIGS. 6 through 8 illustrate the mass spectra of valine at dilutions of 1:10, 1:100, and 1:1000 respectively. These figures illustrate that even at an injected sample amount of 28 femtomoles (FIG. 8), that valine can still be clearly identified.

Example 4

Automated Sequence Analysis Of A Peptide Utilizing PETMA-PITC

A peptide was covalently attached to a Sequelon membrane (Milligen/Biosearch, Burlington, Mass.) using the water soluble carbodiimide 1-ethyl-3-(3-dimethylamine propyl carbodiimide HCl (EDC) (Sigma), Aebersold et al., Anal. Biochem. 187:56–65 (1990). Briefly, peptide solution was applied to 1-cm circular disks of Sequelon membrane in 5 μl aliquots and dried with a stream of air. Peptides were applied either in aqueous solution or in HPLC elution buffer, typically 0.1% TFA in $H_2O/CH_3CN$. A fresh solution of EDC (20 mg/ml in $H_2O$, w/v) was prepared immediately before use. Thirty microliters of the buffer 200 mM MES, pH 4.8 and 10 μl of EDC solution were applied to the dry disk. The buffer for standard coupling conditions was 200 mM MES, pH4.5. The coupling reaction was allowed to proceed for 30–60 minutes at 37° C., then the disk was extensively washed with distilled $H_2O$ to remove excess EDC and any noncoupled peptide.

The following reagents are utilized in automated sequence analysis:

Washing solvent #1: 50% methanol and 50% water
Washing solvent #2: 100% acetone
Coupling base: 5% N-ethyl morpholine in methanol: $H_2O$ (75.25)

PETMA-PITC: 5% by weight in water
Transfer solution: 100% water or 10% acetonitrile
Cleavage solution: 100% TFA
Conversion compound: 20% trifluoroacetic acid in water.

The membrane with peptide attached was first washed with 1 ml of washing solvent #1 and 1 ml of #2, and dried with argon gas. A mixture containing 50 μl of coupling base and 50 μl of PETMA-PITC was delivered to the membrane, which was then incubated for 5 minutes at 50° C. Another 100 μl of the mixture (coupling base and PETMA-PITC) was once again delivered to the membrane (displacing the first), and incubated for 5 minutes at 50° C. The membrane was then washed extensively with solvent #1 for two minutes at a rate of 200 μl per minute. The membrane was then washed with solvent #2 for two minutes at a rate of 200 μl per minute. The membrane was then dried with argon gas. One hundred microliters of cleavage solution was then delivered to the membrane, which was then incubated for 3 minutes at 50° C. Displaced cleavage solution containing the derivatized amino acid was then transferred to a conversion flask, and dried with argon gas. The solid was then redissolved in 50 μl of conversion compound, and incubated for 15 minutes at 60° C., and once again dried down with argon gas. The final product was redissolved in 200 μl of transfer solution, and injected into an RP-HPLC.

When a HPLC separation step is utilized prior to mass spectrometry, amino acids with identical molecular weights such as leucine and isoleucine, may be distinguished. Subsequent to HPLC separation, the sample is analyzed by ion spray mass-spectrometry in a SCIEX model API III triple quadrupole mass spectrometer equipped with an ion spray ion source.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for determining the terminal amino acid of a substantially pure polypeptide, comprising:
    (a) attaching the polypeptide to a solid support;
    (b) reacting the polypeptide with a compound comprising an isothiocyanate group, an ionizable group capable of detection by mass spectrometry, and a linker connecting the isothiocyanate group with the ionizable group, under conditions and for a time sufficient for coupling to occur between the terminal amino acid of the polypeptide and the compound, thereby yielding a polypeptide with a derivatized terminal amino acid;
    (c) washing the solid support to remove unbound material;
    (d) cleaving the derivatized terminal amino acid from the polypeptide with a cleaving agent;
    (e) ionizing the cleaved derivatized terminal amino acid; and
    (f) determining the molecular weight of the derivatized terminal amino acid, such that said terminal amino acid is determined.

2. The method of claim 1, subsequent to the step of determining the molecular weight of the derivatized terminal amino acid, repeating steps (b) through (f) such that the next amino acid is determined.

3. The method of claim 1 wherein the molecular weight of the derivatized terminal amino acid is determined in an ion-spray mass spectrometer.

4. The method of claim 1, subsequent to the step of cleaving, separating the derivatized terminal amino acid such that derivatized amino acids with identical molecular weights are separated.

5. A method for determining the amino acid sequence of a substantially pure polypeptide, comprising:
    (a) attaching the polypeptide to a solid support;
    (b) reacting the polypeptide with a compound comprising an isothiocyanate group, an ionizable group capable of detection by mass spectrometry, and a linker connecting the isothiocyanate group with the ionizable group, under conditions and for a time sufficient for coupling to occur between the

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear     ( i i ) MOLECULE TYPE: peptide     ( i i i ) HYPOTHETICAL: YES     ( i v ) ANTI-SENSE: NO     ( v ) FRAGMENT TYPE: N-terminal     ( x i ) SEQUENCE DESCRIPTION: SEQ ID NO:1:

Val Gln Ala Ala Ile Asp Tyr Ile Asp Gly
1               5                   10 terminal amino acid of the polypeptide and the compound, thereby yielding a polypeptide with a derivatized terminal amino acid;

(c) washing the solid support to remove unbound material;

(d) cleaving the derivatized terminal amino acid from the polypeptide with a cleaving agent;

(e) ionizing the cleaved derivatized terminal amino acid;

(f) determining the molecular weight of the derivatized terminal amino acid; and (g) repeating steps (b) through (f) as recited above in order to determine the amino acid sequence of said polypeptide.

* * * * *